US012729172B2

(12) United States Patent
Noguchi et al.

(10) Patent No.: US 12,729,172 B2
(45) Date of Patent: Sep. 8, 2026

(54) METHOD FOR PRODUCING PURIFIED TRANS-1,2-DIFLUOROETHYLENE (HFO-1132(E)) AND/OR 1,1,2-TRIFLUOROETHYLENE (HFO-1123)

(71) Applicant: DAIKIN INDUSTRIES, LTD., Osaka (JP)

(72) Inventors: Atsushi Noguchi, Osaka (JP); Tatsuya Takakuwa, Osaka (JP); Akikazu Tabuchi, Osaka (JP)

(73) Assignee: DAIKIN INDUSTRIES, LTD., Osaka (JP)

(*) Notice: Subject to any disclaimer, the term of this patent is extended or adjusted under 35 U.S.C. 154(b) by 809 days.

(21) Appl. No.: 18/084,715

(22) Filed: Dec. 20, 2022

(65) Prior Publication Data

US 2023/0150902 A1 May 18, 2023

Related U.S. Application Data

(63) Continuation of application No. PCT/JP2021/021038, filed on Jun. 2, 2021.

(30) Foreign Application Priority Data

Jun. 22, 2020 (JP) ................................ 2020-106757

(51) Int. Cl.

*C07C 17/386* (2006.01)
*C07C 17/383* (2006.01)
*C09K 5/04* (2006.01)

(52) U.S. Cl.

CPC .......... *C07C 17/386* (2013.01); *C07C 17/383* (2013.01); *C09K 5/045* (2013.01);

(Continued)

(58) Field of Classification Search

CPC ..... C07C 17/38; C07C 17/383; C07C 17/386; B01D 3/34; B01D 3/36; B01D 3/40

See application file for complete search history.

(56) References Cited

U.S. PATENT DOCUMENTS 3,101,304 A * 8/1963 Wiist .................... C07C 17/386 203/67
4,898,645 A * 2/1990 Voigt ...................... C07C 17/38 203/67

(Continued)

FOREIGN PATENT DOCUMENTS

CN 101219926 A * 7/2008 ........... C07C 17/386
CN 106316779 A * 1/2017 ........... C07C 17/383

(Continued)

OTHER PUBLICATIONS

Luyben ("Comparison of extractive distillation and pressure-swing distillation for acetone-methanol separation", Ind. Eng. Chem. Res., 2008, 47, 2696-2707) (Year: 2008).*

(Continued)

*Primary Examiner* — Matthew R Diaz
(74) *Attorney, Agent, or Firm* — Wenderoth, Lind & Ponack, L.L.P.

(57) ABSTRACT

The present disclosure provides a method for producing purified trans-1,2-difluoroethylene (HFO-1132(E)) and/or 1,1,2-trifluoroethylene (HFO-1123), comprising a distillation step of distilling composition 1 comprising difluoromethane (HFC-32) and HFO-1132(E) and/or HFO-1123 to obtain composition 2 in which HFC-32 is reduced from composition 1; and an extractive distillation step of bringing composition 2 into contact with an extraction solvent to obtain a composition comprising HFO-1132(E) and/or HFO-1123, in which HFC-32 is reduced from composition 2, composition 2 being an azeotropic composition or azeo- (Continued)

trope-like composition comprising HFC-32 and HFO-1132 (E) and/or HFO-1123.

12 Claims, 5 Drawing Sheets

(52) U.S. Cl.
CPC .... *C09K 2205/126* (2013.01); *C09K 2205/22* (2013.01); *C09K 2205/32* (2013.01)

(56) References Cited

U.S. PATENT DOCUMENTS

| | | | | |
|---|---|---|---|---|
| 5,182,040 | A * | 1/1993 | Bartlett | C09K 5/045 252/364 |
| 6,337,033 | B2 * | 1/2002 | Basile | C09K 5/045 252/68 |
| 7,699,962 | B2 * | 4/2010 | McDonald | B01D 3/36 203/67 |
| 9,023,233 | B2 * | 5/2015 | Furuta | C07C 17/383 570/178 |
| 10,081,749 | B2 * | 9/2018 | Taniguchi | C07C 17/383 |
| 2003/0116422 | A1 * | 6/2003 | Boehmer | C07C 17/386 203/57 |
| 2016/0244653 | A1 * | 8/2016 | Singh | C09K 5/045 |
| 2017/0002245 | A1 * | 1/2017 | Fukushima | C09K 5/045 |
| 2018/0155259 | A1 * | 6/2018 | Ohkubo | C07C 17/383 |

FOREIGN PATENT DOCUMENTS

| | | | | |
|---|---|---|---|---|
| JP | 7-291878 | | 11/1995 | |
| JP | H07291878 | A * | 11/1995 | C07C 17/386 |
| JP | 2001-513520 | | 9/2001 | |
| JP | 2013-241348 | | 12/2013 | |
| JP | 2016023145 | A * | 2/2016 | C07C 17/383 |
| JP | 2016-130236 | | 7/2016 | |
| WO | 2009/010472 | | 1/2009 | |
| WO | 2015/141678 | | 9/2015 | |
| WO | WO-2015141678 | A1 * | 9/2015 | C09K 5/04 |

OTHER PUBLICATIONS

Speight ("The chemistry and technology of petroleum", fifth edition, 2014, 475-478) (Year: 2014).*

Nancy Medina-Herrera, et al., "An Approach for Solvent Selection in Extractive Distillation Systems Including Safety Considerations", Industrial & Engineering Chemistry Research, 2014, vol. 53, pp. 12023-12031.

International Search Report issued Aug. 24, 2021 in corresponding International Application No. PCT/JP2021/021038.

OECC Newsletter, "2. (3) Chlorofluorocarbon Separator", 2018, No. 83, pp. 15-17, with partial English translation, cited in ISR.

Extended European Search Report issued Jun. 20, 2024 in European Patent Application No. 21828570.8.

International Preliminary Report on Patentability issued Dec. 13, 2022 in International (PCT) Application No. PCT/JP2021/021038.

* cited by examiner

METHOD FOR PRODUCING PURIFIED TRANS-1,2-DIFLUOROETHYLENE (HFO-1132(E)) AND/OR 1,1,2-TRIFLUOROETHYLENE (HFO-1123)

TECHNICAL FIELD

The present disclosure relates to a method for producing purified trans-1,2-difluoroethylene (HFO-1132(E)) and/or 1,1,2-trifluoroethylene (HFO-1123).

BACKGROUND ART

HFO-1132(E) is attracting attention as a refrigerant that can replace the greenhouse gases difluoromethane (HFC-32) and 1,1,1,2,2-pentafluoroethane (HFC-125) because of its low global warming potential (GWP).

PTL 1 discloses a method for producing 1,2-difluoroethylene from a compound represented by formula (1): $CH_2FX$ (1) (X is a halogen atom) by a synthesis reaction accompanying pyrolysis.

PTL 2 discloses a method for producing 1,1,2-trifluoroethylene (HFO-1123) by dehydrofluorination of 1,1,1,2-tetrafluoroethane (HFC-134a).

CITATION LIST

Patent Literature

PTL 1: JP2013-241348A
PTL 2: WO2009/010472

SUMMARY

The present disclosure includes, for example, the invention described in the following.

A method for producing purified trans-1,2-difluoroethylene (HFO-1132(E)) and/or 1,1,2-trifluoroethylene (HFO-1123), comprising:

- a distillation step of distilling composition 1 comprising difluoromethane (HFC-32) and HFO-1132(E) and/or HFO-1123 to obtain composition 2 in which HFC-32 is reduced from composition 1; and
- an extractive distillation step of bringing composition 2 into contact with an extraction solvent to obtain a composition comprising HFO-1132(E) and/or HFO-1123, in which HFC-32 is reduced from composition 2,
- composition 2 being an azeotropic composition or azeotrope-like composition comprising HFC-32 and HFO-1132(E) and/or HFO-1123.

Advantageous Effects

The present disclosure makes it possible to efficiently purify HFO-1132(E) and/or HFO-1123.

DESCRIPTION OF EMBODIMENTS

Figure 1:
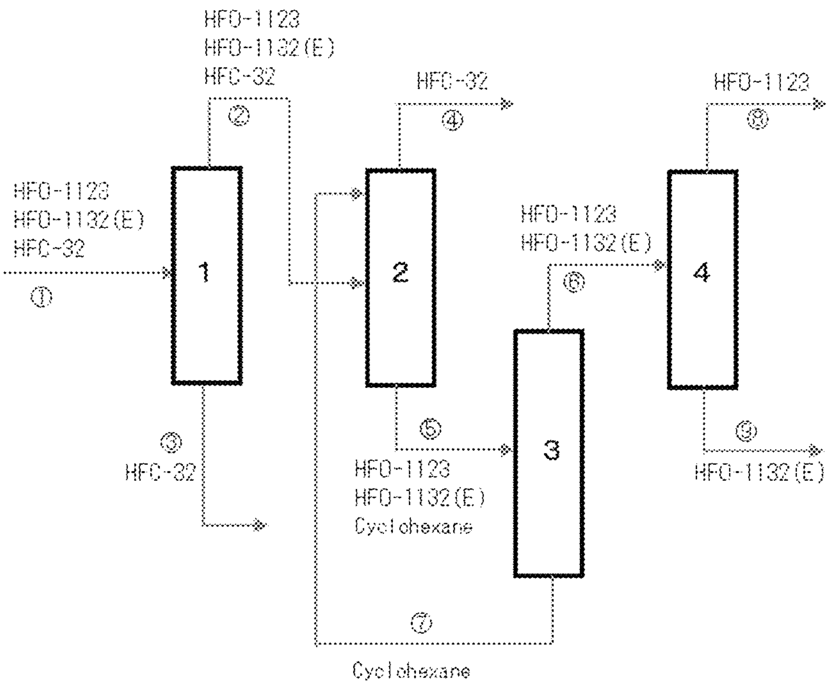
FIG. 1 is the outline of the process in Example 1.

As a result of extensive research, the present inventors found that a composition comprising HFC-32 and HFO-1132(E) and/or HFO-1123 can be distilled and then brought into contact with an extraction solvent, thereby efficiently purifying HFO-1132(E) and/or HFO-1123.

The present disclosure has been completed as a result of further research based on this finding.

In the present specification, a numerical range expressed using "to" refers to a range that includes the numerical values described before and after "to" as the lower and upper limit values.

In the present specification, an azeotropic composition refers to a composition that behaves as if it were a single substance with no difference in composition between the liquid phase and the gas phase under constant pressure.

In the present specification, an azeotrope-like composition refers to a composition that can form azeotropic composition, and that has composition close to azeotropic composition and behavior like an azeotropic composition. The azeotrope-like composition can be distilled and/or refluxed with little change in composition. Therefore, the azeotrope-like composition can be treated almost the same as the azeotropic composition.

In the present specification, the standard boiling point refers to the boiling point at a standard atmospheric pressure of 1013.25 hPa.

In the present specification, the gauge pressure refers to a relative pressure based on the atmospheric pressure, meaning the pressure difference obtained by subtracting the atmospheric pressure from the absolute pressure.

In the present specification, the "purity" of the refrigerant refers to the component ratio (mol %) determined by quantitative analysis using gas chromatography.

In the present specification, the main component refers to a component preferably contained in an amount of 85 mol % to 99.9 mol %, more preferably 90 mol % to 99.9 mol %, even more preferably 95 mol % to 99.9 mol %, and particularly preferably 99 mol % to 99.9 mol %.

In the present specification, extractive distillation refers to a distillation operation to add an extraction solvent to a mixture consisting of two or three components that have very similar standard boiling points and are difficult to separate by ordinary distillation, and having a specific volatility (relative volatility) close to 1, or a combination mixture with azeotropic composition, to form an extraction mixture, and facilitate separation by adjusting the relative volatility of the original two or three components away from 1. When the relative volatility is 1, separation by distillation is impossible.

The present disclosure includes the following embodiments.

Production Method 1

Production method 1 of the present disclosure is a method for producing purified HFO-1132(E) and/or HFO-1123, comprising, in this order:

- a distillation step of distilling composition 1 comprising HFC-32 and HFO-1132(E) and/or HFO-1123 to obtain composition 2 in which HFC-32 is reduced from composition 1; and
- an extractive distillation step of bringing composition 2 obtained in the distillation step into contact with an extraction solvent to obtain a composition comprising HFO-1132(E) and/or HFO-1123, in which HFC-32 is reduced from composition 2.

In production method 1, composition 2 obtained in the distillation step is an azeotropic composition or azeotrope-like composition comprising HFC-32 and HFO-1132(E) and/or HFO-1123.

Production Method 2

Production method 2 of the present disclosure is a method for producing purified HFO-1132(E) and/or HFO-1123, comprising an extractive distillation step of bringing an azeotropic composition or azeotrope-like composition comprising HFC-32 and HFO-1132(E) and/or HFO-1123 into contact with an extraction solvent to obtain a composition in which HFC-32 is reduced from the azeotropic composition or the azeotrope-like composition.

Distillation Step

The distillation step of production method 1 is a step of distilling composition 1 comprising HFC-32 and HFO-1132 (E) and/or HFO-1123 (hereinafter also referred to as "the distillation composition") to obtain composition 2 in which HFC-32 is reduced from composition 1. In other words, the distillation step is a step of distilling the distillation composition to reduce the content of HFC-32 in the distillation composition.

The term "reduce" in the distillation step means to reduce the content of a compound in the distillation composition. For example, the content of HFC-32 in the distillation composition is reduced to reduce the absolute amount to be subjected to extractive distillation in the extractive distillation step of production method 1, which can save the energy costs.

In the distillation step, from the viewpoint of saving the energy costs, the content of HFC-32 in composition 1 is preferably reduced by 80 mass % or more, more preferably 85 mass % or more, even more preferably 90 mass % or more, and particularly preferably 95 mass % or more.

HFC-32 (standard boiling point: −51.7° C.) and HFO-1123 (standard boiling point: −60° C.) are azeotropic or azeotrope-like, and an azeotropic composition or azeotrope-like composition of HFO-1123 and HFC-32 has a boiling point at a temperature (−61.4° C.) lower than the boiling points of both HFO-1123 and HFC-32. In the distillation step of production method 1, taking advantage of this property, an azeotropic composition or azeotrope-like composition of HFC-32, HFO-1123, and HFC-32 is separated by distillation in a distillation column.

Further, HFC-32 and HFO-1132(E) (standard boiling point: −53° C.) are azeotropic or azeotrope-like, and an azeotropic composition or azeotrope-like composition of HFC-32 and HFO-1132(E) has a boiling point at a temperature (−54.8° C.) lower than the boiling points of both HFC-32 and HFO-1132(E). In the distillation step of production method 1, taking advantage of this property, an azeotropic composition or azeotrope-like composition of HFC-32, HFO-1123, and HFC-32 is separated by distillation in the distillation column.

Composition 1 preferably contains HFC-32, HFO-1132 (E), and HFO-1123. In this case, HFC-32, HFO-1132(E), and HFO-1123 form an azeotrope, and an azeotropic composition or azeotrope-like composition of HFC-32, HFO-1132(E), and HFO-1123 boils at a temperature ranging from the boiling point temperature of an azeotropic composition or azeotrope-like composition of HFO-1123 and HFC-32 to the boiling point temperature of an azeotropic composition or azeotrope-like composition of HFO-1132(E) and HFC-32. In the distillation step of production method 1, taking advantage of this property, an azeotropic composition or azeotrope-like composition of HFC-32, HFO-1132(E), HFO-1123, and HFC-32 is separated by distillation in the distillation column.

Distillation in the distillation step of production method 1 is preferably azeotropic distillation.

Composition 1 contains HFC-32 and HFO-1132(E) and/or HFO-1123 in such amounts that the sum of the concentrations of these components is preferably 99.5 mass % or more, more preferably 99.7 mass % or more, even more preferably 99.8 mass % or more, and still even more preferably 99.9 mass % or more.

Composition 1 preferably contains HFC-32, HFO-1132 (E), and HFO-1123. In this case, composition 1 contains HFO-1123, HFO-1132(E), and HFC-32 in such amounts that the sum of the concentrations of these components is preferably 99.5 mass % or more, more preferably 99.7 mass % or more, even more preferably 99.8 mass % or more, and still even more preferably 99.9 mass % or more.

Composition 1 preferably consists of HFO-1123, HFO-1132(E), and/or HFC-32. Composition 1 may contain inevitable impurities.

Composition 1 particularly preferably consists of HFO-1132(E), HFO-1123, and HFC-32. Composition 1 may contain inevitable impurities.

The number of theoretical plates of the distillation column used in the distillation step is preferably 10 or more, and more preferably 20 or more. The number of theoretical plates of the distillation column used in the distillation step is preferably 60 or less, and more preferably 50 or less, from an economic viewpoint.

In the distillation step, the distillation composition is preferably supplied to a middle portion of the distillation column.

In the distillation step, the pressure at which distillation is performed is preferably 0.05 to 5 MPaG (gauge pressure). The lower limit value of the pressure at which distillation is performed is preferably 0.05 MPaG, more preferably 0.1 MPaG, even more preferably 0.25 MPaG, and particularly preferably 0.5 MPaG. The upper limit value of the pressure at which distillation is performed is preferably 5 MPaG, more preferably 4 MPaG, even more preferably 3 MPaG, and particularly preferably 2 MPaG.

The amount of HFC-32 supplied in the distillation step is generally 1 to 500 mol, preferably 5 to 400 mol, and more preferably 10 to 300 mol, per mol of HFO-1123 supplied to the distillation column.

The distillation composition is, for example, a composition using HFC-32 as a raw material and obtained in the production of HFO-1132(E). Specific examples of the distillation composition include a composition containing reaction products HFO-1123 and HFO-1132(E), and unreacted HFC-32, in a reaction gas containing HFO-1132(E) obtained by subjecting HFC-32 to a pyrolysis reaction.

The reflux ratio of the distillation column is not limited, but is preferably 1 to 300, and more preferably 10 to 200.

The distillation step can be performed by a discontinuous operation or a continuous operation; the step is preferably performed by a continuous operation from an industrial viewpoint.

Composition 2 obtained in the distillation step is obtained as a distillate from the top of the distillation column by distilling the distillation composition. Composition 2 is supplied as an extractive distillation composition to an extractive distillation step described below.

The content of HFC-32 in composition 2 relative to the content of HFC-32 in composition 1 is preferably 5 mass % or less, and more preferably 3 mass % or less. The lower limit value is preferably 0.5 mass % or more, and more preferably 1 mass % or more.

Composition 2 is preferably an azeotropic composition or azeotrope-like composition comprising HFC-32, HFO-1132 (E), and HFO-1123.

Extractive Distillation Step

The extractive distillation step of production method 1 is a step of bringing composition 2 into contact with an extraction solvent to obtain a composition comprising HFO-1132(E) and/or HFO-1123, in which HFC-32 is reduced from composition 2. In other words, the extractive distillation step of production method 1 is a step of subjecting composition 2 obtained in the distillation step to extractive distillation in the presence of an extraction solvent to obtain a composition comprising HFO-1132(E) and/or HFO-1123, in which HFC-32 is reduced from composition 2.

The extractive distillation step of production method 1 is preferably a step of bringing composition 2 into contact with an extraction solvent to obtain a composition comprising HFO-1132(E) and/or HFO-1123, and not substantially comprising HFC-32. The extractive distillation step of production method 1 is preferably a step of bringing composition 2 into contact with an extraction solvent to obtain a composition comprising HFO-1132(E) and HFO-1123, and not substantially comprising HFC-32.

The extractive distillation step of production method 2 is a step of bringing an azeotropic composition or azeotrope-like composition comprising HFC-32 and HFO-1132(E) and/or HFO-1123 into contact with an extraction solvent to obtain a composition in which HFC-32 is reduced from the azeotropic composition or the azeotrope-like composition. In other words, the extractive distillation step of production method 2 is a step of subjecting an azeotropic composition or azeotrope-like composition comprising HFC-32 and HFO-1132(E) and/or HFO-1123 to extractive distillation in the presence of an extraction solvent to obtain a composition in which HFC-32 is reduced from the azeotropic composition or the azeotrope-like composition.

The azeotropic composition or azeotrope-like composition in production method 2 contains HFC-32 and HFO-1132(E) and/or HFO-1123 in such amounts that the sum of the concentrations of these components is preferably 99.5 mass % or more, more preferably 99.7 mass % or more, even more preferably 99.8 mass % or more, and still even more preferably 99.9 mass % or more.

The azeotropic composition or azeotrope-like composition in production method 2 preferably contains HFC-32, HFO-1132(E), and HFO-1123. In this case, the azeotropic composition or azeotrope-like composition in production method 2 contains HFO-1123, HFO-1132(E), and HFC-32 in such amounts that the sum of the concentrations of these components is preferably 99.5 mass % or more, more preferably 99.7 mass % or more, even more preferably 99.8 mass % or more, and still even more preferably 99.9 mass % or more.

The azeotropic composition or azeotrope-like composition in production method 2 more preferably consists of HFO-1123, HFO-1132(E), and/or HFC-32. The azeotropic composition or azeotrope-like composition in production method 2 may contain inevitable impurities.

The extractive distillation step of production method 2 is preferably a step of bringing an azeotropic composition or azeotrope-like composition comprising HFC-32 and HFO-1132(E) and/or HFO-1123 into contact with an extraction solvent to obtain a composition comprising HFO-1132(E) and/or HFO-1123, and not substantially comprising HFC-32. The extractive distillation step of production method 2 is more preferably a step of bringing an azeotropic composition or azeotrope-like composition comprising HFC-32 and HFO-1132(E) and/or HFO-1123 into contact with an extraction solvent to obtain a composition comprising HFO-1132 (E) and HFO-1123, and not substantially comprising HFC-32.

Production methods 1 and 2 of the present disclosure have an extractive distillation step in common. In the present specification, the extractive distillation step of production methods 1 and 2 of the present disclosure is also referred to as "the extractive distillation step of the present disclosure."

In the present specification, "not substantially comprising HFC-32" means that the content of HFC-32 in the composition obtained in the extractive distillation step of production methods 1 and 2 is preferably less than 1 mass %, more preferably less than 0.5 mass %, and particularly preferably less than 0.1%.

In the extractive distillation step of the present disclosure, the extraction solvent is preferably at least one compound selected from the group consisting of saturated hydrocarbon compounds, halogenated hydrocarbon compounds, nitrile compounds, ether compounds, ketone compounds, alcohol compounds, and ester compounds.

Examples of saturated hydrocarbon compounds include n-pentane, n-hexane, n-heptane, n-octane, cyclopentane, cyclohexane, cycloheptane, benzene, toluene, and the like. Preferred among these is cyclohexane.

Examples of halogenated hydrocarbon compounds include dichloromethane, trichloromethane, tetrachloromethane (carbon tetrachloride), 1,1-dichloroethane, 1,2-dichloroethane, 1,1,1-trichloroethane, 1,1,2-trichloroethane, and the like. Preferred among these is carbon tetrachloride.

Examples of nitrile compounds include acetonitrile, propanenitrile, isobutyronitrile, and the like. Preferred among these is acetonitrile.

Examples of ether compounds include di-n-propyl ether, diisopropyl ether, 2-methoxy-2-methylpropane, 2-ethoxy-2-methylpropane, and the like. Preferred among these is di-n-propyl ether.

Examples of ketone compounds include acetone, diethyl ketone, methyl ethyl ketone, methyl isobutyl ketone, cyclopentanone, and the like. Preferred among these is acetone.

Examples of alcohol compounds include methanol, ethanol, 1-propanol, 2-propanol, 1-butanol (n-butyl alcohol), 2-methyl-1-propanol (i-butyl alcohol), 2-butanol (sec-butyl alcohol), 2-methyl-2-propanol (t-butyl alcohol), and the like. Preferred among these is methanol.

Examples of ester compounds include methyl acetate, ethyl acetate, propyl acetate, isopropyl acetate, butyl acetate, and the like. Preferred among these is ethyl acetate.

These extraction solvents can be used singly or in combination of two or more.

In the extractive distillation step of the present disclosure, the extraction solvent is more preferably at least one member selected from the group consisting of cyclohexane, carbon tetrachloride, acetonitrile, di-n-propyl ether, acetone, methanol, and ethyl acetate; and particularly preferably cyclohexane and acetonitrile.

Regarding the temperature range of the standard boiling point in the extractive distillation step of the present disclosure, the temperature difference may be of a degree such that the extraction solvent can be separated from the compound to be separated in the extractive distillation step by simple distillation, stripping, or the like; i.e., the temperature difference is generally 20° C. or more. However, if the standard boiling point is too high, the extraction solvent itself may be decomposed. Therefore, the standard boiling point of the extraction solvent is preferably 30 to 135° C., more preferably 35 to 120° C., even more preferably 40 to 100° C., and particularly preferably 50 to 90° C., from the viewpoint of efficiently performing extractive distillation.

The amount of the extraction solvent used in production methods 1 and 2 is preferably 1 equivalent or more and 20 equivalents or less, per equivalent of the composition supplied to an extractive distillation column.

In production methods 1 and 2, the concentration (purity) of HFC-32 in the composition to be subjected to extractive distillation is preferably 50 mol % or less, and more preferably 25 mol % or less.

The number of theoretical plates of the extractive distillation column used in the extractive distillation step of the present disclosure is preferably 10 or more, and more preferably 20 or more. The number of theoretical plates of the extractive distillation column used in the extractive distillation step is preferably 60 or less, and more preferably 50 or less, from an economic viewpoint.

In the extractive distillation step of the present disclosure, the extraction solvent is preferably supplied to an upper portion of the extractive distillation column. The extraction solvent used in the extractive distillation step of the present disclosure is preferably the extraction solvent that is recovered in the extraction solvent recovery step of the present disclosure and recirculated. The reflux ratio of the extractive distillation column is not limited, but is preferably 1 to 20, and more preferably 3 to 10.

In the extractive distillation step of the present disclosure, the pressure at which extractive distillation is performed is preferably 0.05 to 5 MPaG (gauge pressure). The lower limit value of the pressure is preferably 0.05 MPaG, more preferably 0.1 MPaG, even more preferably 0.25 MPaG, and particularly preferably 0.5 MPaG. The upper limit value of the pressure is preferably 5 MPaG, more preferably 4 MPaG, even more preferably 3 MPaG, and particularly preferably 2 MPaG.

The extractive distillation step of the present disclosure can be performed by a discontinuous operation or a continuous operation; the step is preferably performed by a continuous operation from an industrial viewpoint. Further, extractive distillation can be repeated to thereby purify the distillate component to a high purity.

In production methods 1 and 2, when HFC-32 is distilled from the azeotropic composition or azeotrope-like composition of HFC-32 and HFO-1123, it is desirable to use an extraction solvent that makes the relative volatility of HFC-32 to HFO-1123 when the extraction solvent is added 1 or more, and preferably 1.2 or more. As a result, the gas-phase mole fraction of HFC-32 increases to increase HFC-32 in the gas phase, HFC-32 can be separated from the top of the extractive distillation column, and the extraction solvent and HFO-1123 are obtained from the bottom of the extractive distillation column.

In production methods 1 and 2, when HFC-32 is distilled from an azeotropic composition or azeotrope-like composition of HFC-32 and HFO-1132(E), it is desirable to use an extraction solvent that makes the relative volatility of HFC-32 to HFO-1132(E) when the extraction solvent is added 1 or more, and preferably 1.2 or more. As a result, the gas-phase mole fraction of HFC-32 increases to increase HFC-32 in the gas phase, HFC-32 can be separated from the top of the extractive distillation column, and the extraction solvent and HFO-1132(E) are obtained from the bottom of the extractive distillation column.

The amount of the extraction solvent used in the extractive distillation step of the present disclosure is preferably 1 equivalent or more and 20 equivalents or less, per equivalent of composition 2.

Rectification Step

Production methods 1 and 2 of the present disclosure have a rectification step in common. In the present specification, the rectification step of production methods 1 and 2 of the present disclosure is also referred to as "the rectification step of the present disclosure."

Production methods 1 and 2 of the present disclosure preferably have a rectification step of rectifying the composition obtained in the extractive distillation step of the present disclosure to separate it into a composition comprising HFO-1132(E) as a main component, and a composition comprising HFO-1123 as a main component.

The rectification step of the present disclosure is a step of rectifying the composition obtained in the extractive distillation step of the present disclosure in a rectification column to separate, from the composition, a composition comprising HFO-1132(E) as a main component, and a composition comprising HFO-1123 as a main component, thereby obtaining purified HFO-1132(E) and purified HFO-1123.

The composition comprising HFO-1132(E) as a main component contains HFO-1132(E) and HFO-1123. In this composition, the ratio (mol %) of HFO-1132(E) based on the total amount of HFO-1132(E) and HFO-1123 is preferably 85 mol % to 99.9 mol %, more preferably 90 mol % to 99.9 mol %, even more preferably 95 mol % to 99.9 mol %, and particularly preferably 99 mol % to 99.9 mol %.

The composition comprising HFO-1123 as a main component contains HFO-1123 and HFO-1132(E). In this composition, the ratio (mol %) of HFO-1123 based on the total amount of HFO-1123 and HFO-1132(E) is preferably 85 mol % to 99.9 mol %, more preferably 90 mol % to 99.9 mol %, even more preferably 95 mol % to 99.9 mol %, and particularly preferably 99 mol % to 99.9 mol %.

The number of theoretical plates of the rectification column used in the rectification step of the present disclosure is preferably 10 or more, and more preferably 20 or more. The number of theoretical plates of the rectification column used in the rectification step of the present disclosure is preferably 60 or less, and more preferably 50 or less, from an economic viewpoint.

In the rectification step of the present disclosure, the composition obtained in the extractive distillation step of the present disclosure is preferably supplied to a middle portion of the rectification column.

In the rectification step of the present disclosure, the pressure at which rectification is performed is preferably 0.05 to 5 MPaG (gauge pressure). The lower limit value of the pressure is preferably 0.05 MPaG, more preferably 0.1 MPaG, even more preferably 0.25 MPaG, and particularly preferably 0.5 MPaG. The upper limit value of the pressure is preferably 5 MPaG, more preferably 4 MPaG, even more preferably 3 MPaG, and particularly preferably 2 MPaG.

The reflux ratio of the rectification column of the present disclosure is not limited, but is preferably 5 to 30, and more preferably 10 to 20.

The rectification step of the present disclosure can be performed by a discontinuous operation or a continuous operation; the step is preferably performed by a continuous operation from an industrial viewpoint.

Production methods 1 and 2 of the present disclosure preferably have the distillation step, the extractive distillation step, and the rectification step in this order.

Extraction Solvent Recovery Step

Production methods 1 and 2 of the present disclosure have an extraction solvent recovery step in common. In the present specification, the extraction solvent recovery step of production methods 1 and 2 of the present disclosure is also referred to as "the extraction solvent recovery step of the present disclosure."

Production methods 1 and 2 of the present disclosure preferably have an extraction solvent recovery step of recovering the extraction solvent used in the extractive distillation step of the present disclosure, and recirculating the recovered extraction solvent to the extractive distillation step.

The number of theoretical plates of an extraction solvent recovery column used in the extraction solvent recovery step of the present disclosure is preferably 5 or more, and more preferably 10 or more. The number of theoretical plates of the extraction solvent recovery column used in the extraction solvent recovery step of the present disclosure is preferably 30 or less, and more preferably 20 or less, from an economic viewpoint.

In the extraction solvent recovery step of the present disclosure, the pressure at which distillation is performed is preferably 0.05 to 5 MPaG (gauge pressure).

The reflux ratio of the extraction solvent recovery column of the present disclosure is not limited, but is preferably 1 to 10, and more preferably 1 to 3.

The extraction solvent recovery step of the present disclosure can be performed by a discontinuous operation or a continuous operation; the step is preferably performed by a continuous operation from an industrial viewpoint.

Production methods 1 and 2 of the present disclosure preferably comprise the distillation step, the extractive distillation step, the rectification step, and the extraction solvent recovery step; and more preferably consist of the distillation step, the extractive distillation step, the rectification step, and the extraction solvent recovery step.

Azeotropic or Azeotrope-Like Composition

The azeotropic or azeotrope-like composition of the present disclosure comprises refrigerant 1.

Refrigerant 1 comprises HFO-1132(E), HFO-1123, and HFC-32 as essential components. In this item, HFO-1132 (E), HFO-1123, and HFC-32 are also referred to below as "the three components."

The total concentration of the three components in the entire refrigerant 1 is 99.5 mass % or more. In other words, refrigerant 1 contains the three components in such amounts that the sum of the concentrations of these components is 99.5 mass % or more.

In refrigerant 1, the mass ratio of the three components in a ternary composition diagram having the three components as vertices falls within a region surrounded by a quadrilateral having the following 4 points as vertices:

point A (HFO-1132(E)/HFO-1123/HFC-32=39.6 mass %/1.5 mass %/58.9 mass %), point B (HFO-1132(E)/HFO-1123/HFC-32=64.5 mass %/1.4 mass %/34.1 mass %), point C (HFO-1132(E)/HFO-1123/HFC-32=0.9 mass %/70.2 mass %/28.9 mass %), and point D (HFO-1132(E)/HFO-1123/HFC-32=0.9 mass %/80.1 mass %/19.0 mass %).

Figure 10:
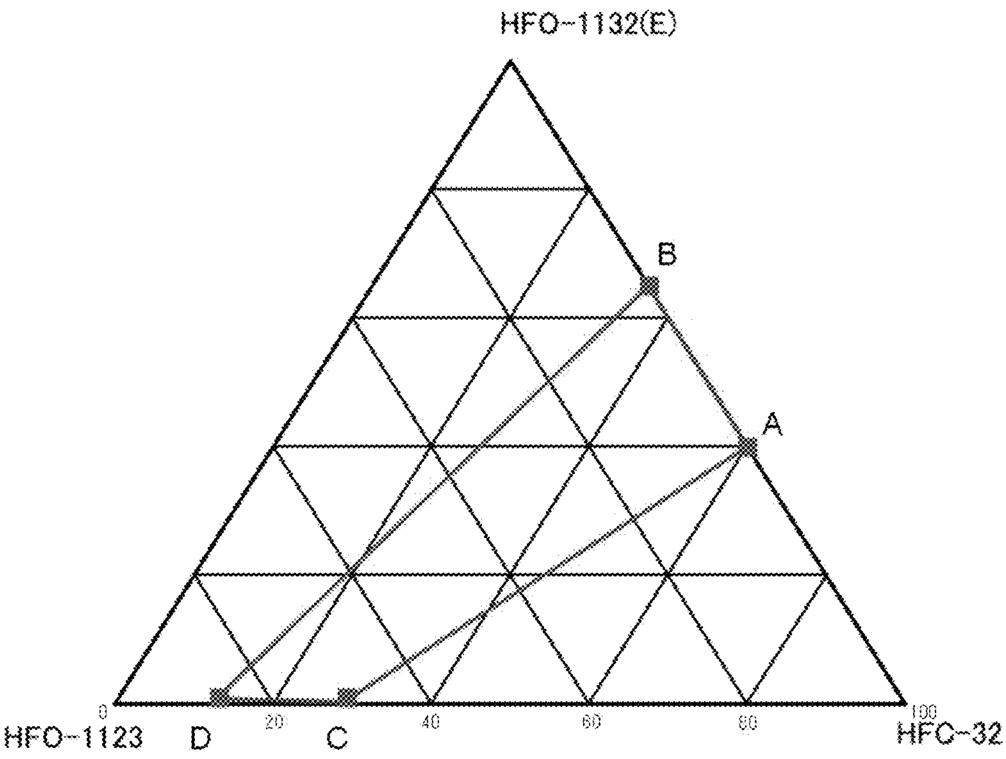
FIG. 10 is a diagram showing the mass ratio of HFO-1132(E), HFO-1123, and HFC-32 (region surrounded by a quadrilateral having 4 points A, B, C, and D as vertices) in a ternary composition diagram of HFO-1132(E), HFO-1123, and HFC-32.

In this item, the ternary composition diagram having the three components as vertices refers to a three-component composition diagram in which the three components (HFO-1132(E), HFO-1123, and HFC-32) are plotted at the vertices of the diagram, and the total concentration of HFO-1132(E), HFO-1123, and HFC-32 is 100 mass %, as shown in FIG. 10.

In the present disclosure, the total concentration of the three components is preferably 99.7 mass % or more, more preferably 99.8 mass % or more, and even more preferably 99.9 mass % or more, based on the entire refrigerant 1.

In the present disclosure, it is particularly preferable that refrigerant 1 consists of HFO-1132(E), HFO-1123, and HFC-32. Refrigerant 1 may contain inevitable impurities.

The azeotropic or azeotrope-like composition of the present disclosure is the same as composition 2 obtained in the distillation step of production method 1.

The azeotropic or azeotrope-like composition of the present disclosure can be used as a raw material for production method 1 of the present disclosure.

The azeotropic or azeotrope-like composition of the present disclosure can be used for producing purified HFO-1132 (E) and/or HFO-1123 in production method 1 of the present disclosure.

The azeotropic or azeotrope-like composition of the present disclosure is an intermediate in production method 1 of the present disclosure.

EXAMPLES

Examples are provided below to specifically describe the present disclosure. However, the present disclosure is not limited to these Examples.

In the Examples, the purity of each component, such as HFO-1132(E), was measured by the following measurement device under the following measurement conditions.

Measurement device: gas chromatograph (using an FID detector) Method for calculating the purity (corresponding to mol % in Tables 1 to 3) of each component:

Purity of *HFO*-1132(*E*)=number of moles of *HFO*-1132(*E*)/(number of moles of *HFO*-1132(*E*)+number of moles of *HFO*-1123+number of moles of *HFC*-32)

Purity of *HFO*-1123=number of moles of *HFO*-1123/(number of moles of *HFO*-1132(*E*)+number of moles of *HFO*-1123+number of moles of *HFC*-32)

Purity of *HFC*-32=number of moles of *HFC*-32/(number of moles of *HFO*-1132(*E*)+number of moles of *HFO*-1123+number of moles of *HFC*-32)

Example 1

According to the flow diagram shown in FIG. 1, purified HFO-1132(E) and HFO-1123 were produced using a composition containing HFO-1123, HFO-1132(E), and HFC-32 as a raw material by a process consisting of a distillation step, an extractive distillation step, an extraction solvent recovery step, and a rectification step. Table 1 below shows the material balance in Example 1.

Distillation Step

A composition containing HFC-32, HFO-1132(E), and HFO-1123 was prepared as a distillation composition. The composition was supplied at a flow rate of 2030 mol/hr to a distillation column having the number of theoretical plates of 40 from the 20th stage from the top of the distillation column. The internal pressure of the distillation column is 0.5 MPaG, the column top is provided with a condenser, and the column bottom is provided with a reboiler.

The reboiler load and condenser load were adjusted so that HFC-32 with a purity of 50.0 mol % was distilled at 59.6 mol/hr from the top of the distillation column, and separation by distillation was performed. At this time, the condenser calorie was calculated to be 40616 kcal/hr, and the reboiler calorie was calculated to be 40617 kcal/hr.

As shown in Table 1, HFC-32 in the composition containing HFO-1123, HFO-1132(E), and HFC-32 was significantly reduced.

Extractive Distillation Step

The distillate (extractive distillation composition) extracted from the top of the distillation column was supplied at a flow rate of 59.6 mol/hr to an extractive distillation column having the number of theoretical plates of 40 from the 20th stage from the top of the extractive distillation column. Further, cyclohexane as an extraction solvent was supplied at a flow rate of 600.0 mol/hr (about 10 equivalents of the flow rate of the extractive distillation composition supplied to the extractive distillation column) to the extractive distillation column from the 5th stage from the top of the extractive distillation column. The internal pressure of the extractive distillation column is 0.5 MPaG, the top of the extractive distillation column is provided with a condenser, and the column bottom is provided with a reboiler.

The reboiler load and condenser load were adjusted so that HFC-32 with a purity of 99.7 mol % was distilled at 29.9 mol/hr from the top of the extractive distillation column, and separation by distillation was performed. At this time, the condenser calorie was calculated to be 273 kcal/hr, and the reboiler calorie was calculated to be 1908 kcal/hr.

Figure 2:
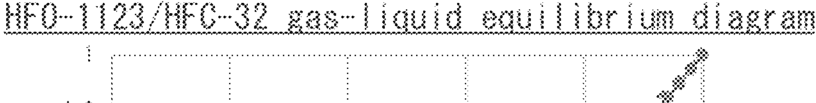
FIG. 2 is an HFO-1123/HFC-32 gas-liquid equilibrium diagram when using cyclohexane as an extraction solvent in the extractive distillation step of Example 1. The horizontal axis indicates the liquid-phase mole fraction of HFO-1123, and the vertical axis indicates the gas-phase mole fraction of HFO-1123.
Figure 2:
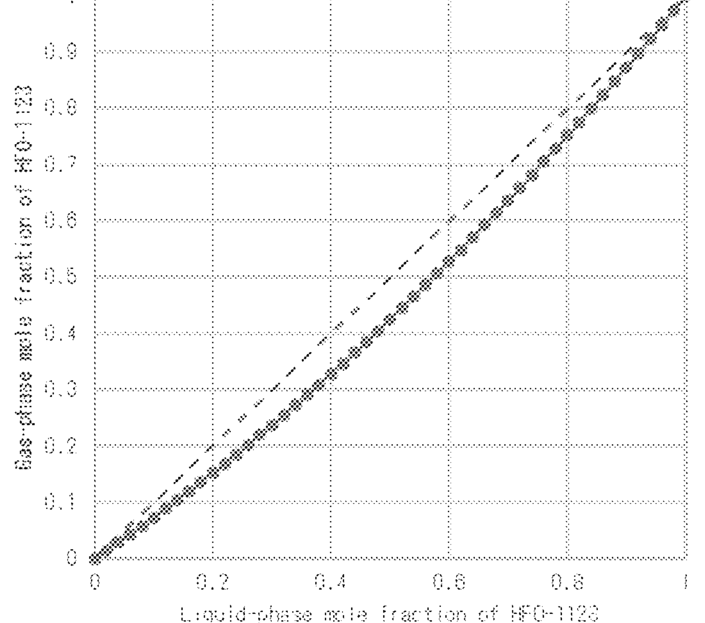

FIG. 2 is an HFO-1123/HFC-32 gas-liquid equilibrium diagram when using about 10 equivalents of cyclohexane as an extraction solvent per equivalent of the extractive distillation composition. As shown in FIG. 2, it was confirmed that HFO-1123 and HFC-32 could be separated by performing a distillation operation at a pressure of 0.5 MPaG using cyclohexane as an extraction solvent.

Figure 3:
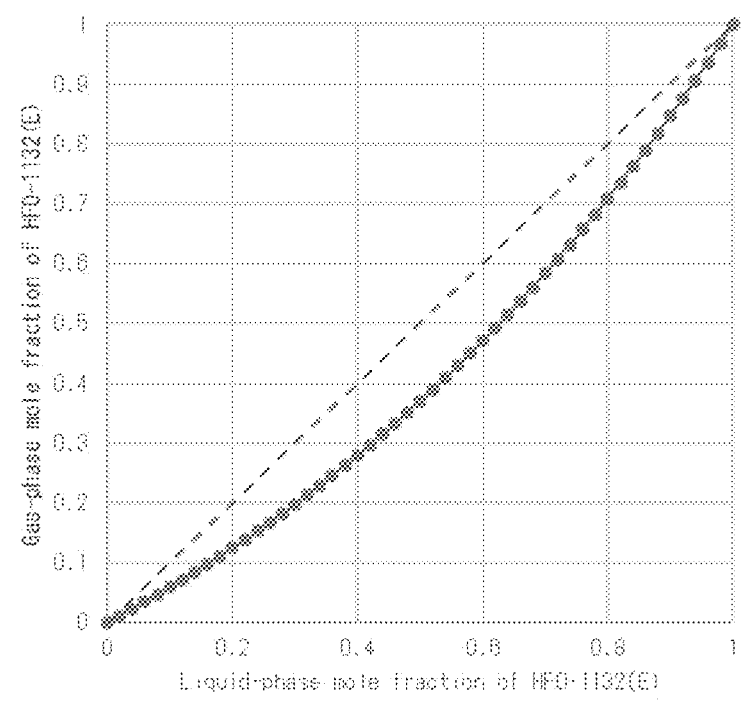
FIG. 3 is an HFO-1132(E)/HFC-32 gas-liquid equilibrium diagram when using cyclohexane as an extraction solvent in the extractive distillation step of Example 1. The horizontal axis indicates the liquid-phase mole fraction of HFO-1132 (E), and the vertical axis indicates the gas-phase mole fraction of HFO-1132(E).

FIG. 3 is an HFO-1132(E)/HFC-32 gas-liquid equilibrium diagram when using about 10 equivalents of cyclohexane as an extraction solvent per equivalent of the extractive distillation composition. As shown in FIG. 3, it was confirmed that HFO-1132(E) and HFC-32 could be separated by performing a distillation operation at a pressure of 0.5 MPaG using cyclohexane as an extraction solvent.

Extraction Solvent Recovery Step

The bottom product extracted from the column bottom in the extractive distillation step was supplied at a flow rate of 629.7 mol/hr (flow rate of HFO-1123: 9.9 mol/hr, flow rate of HFO-1132(E): 19.8 mol/hr, and flow rate of cyclohexane: 600.0 mol/hr) to an extraction solvent recovery column having the number of theoretical plates of 10 (hereinafter simply referred to as "the recovery column") from the 5th stage from the top of the recovery column. The internal pressure of the recovery column is 0.5 MPaG, the column top is provided with a condenser, and the column bottom is provided with a reboiler.

The reboiler load and condenser load were adjusted so that a composition containing HFO-1123 with a purity of 33.4 mol % and HFO-1132(E) with a purity of 66.5 mol % was distilled at 29.7 mol/hr from the top of the recovery column, and separation by distillation was performed. At this time, the condenser calorie was calculated to be 273 kcal/hr, and the reboiler calorie was calculated to be 1908 kcal/hr.

The bottom product containing cyclohexane extracted from the bottom of the recovery column (flow rate of cyclohexane: 600.0 mol/hr) was recirculated to the extractive distillation step for use.

Rectification Step

The distillate extracted from the top of the recovery column was supplied at a flow rate of 29.7 mol/hr to a rectification column having the number of theoretical plates of 40 from the 20th stage from the top of the rectification column. The internal pressure of the rectification column is 0.5 MPaG, the column top is provided with a condenser, and the column bottom is provided with a reboiler.

The reboiler load and condenser load were adjusted so that HFO-1123 with a purity of 90.6 mol % was distilled at 10.8 mol/hr from the top of the rectification column, and rectification was performed. At this time, the condenser calorie was calculated to be 938 kcal/hr, and the reboiler calorie was calculated to be 945 kcal/hr.

The results of the composition analysis of the obtained bottom product by gas chromatography revealed that HFO-1132(E) with a purity of 99.5 mol % was contained.

TABLE 1

| | ① | ② | ④ | ⑥ | ⑧ | ⑨ |
|---|---|---|---|---|---|---|
| Flow rate (mol/hr) | 2030 | 59.6 | 29.9 | 29.7 | 10.8 | 18.9 |
| Purity of HFO-1123 (mol %) | 0.5 | 16.8 | 0.3 | 33.4 | 90.6 | 0.5 |
| Purity of HFO-1132 (E) (mol %) | 1.0 | 33.2 | 0.0 | 66.5 | 9.1 | 99.5 |
| Purity of HFC-32 (mol %) | 98.5 | 50.0 | 99.7 | 0.1 | 0.3 | 0.0 |

Example 2

Figure 4:
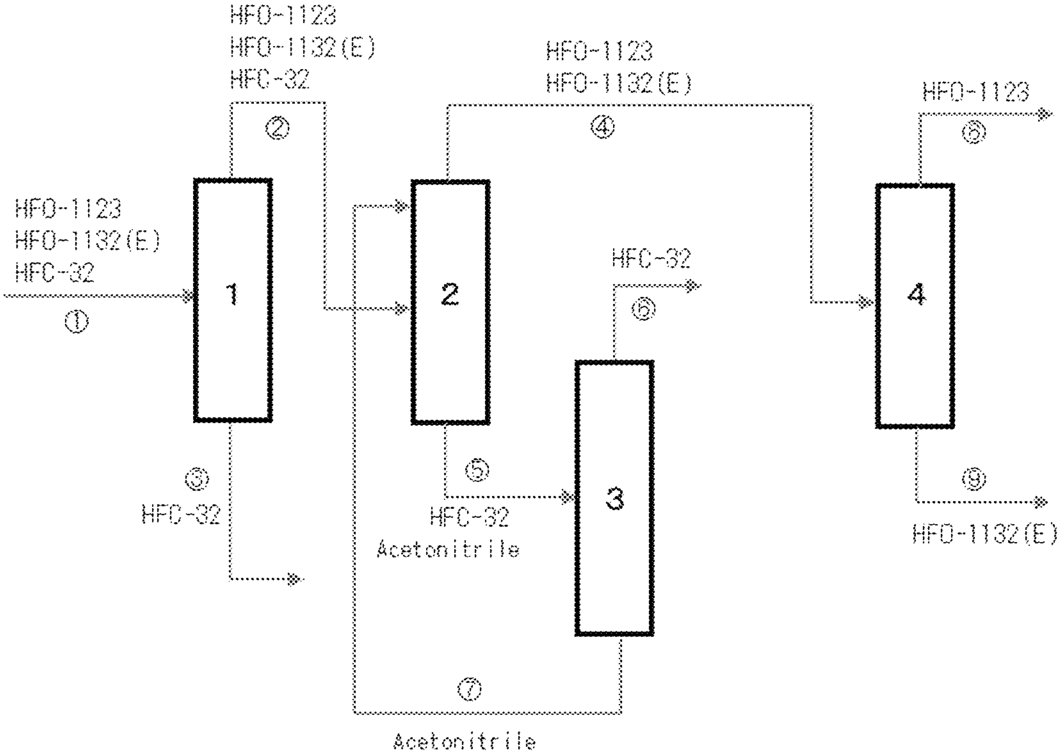
FIG. 4 is the outline of the process in Example 2.

According to the flow diagram shown in FIG. 4, purified HFO-1132(E) and HFO-1123 were produced using a composition containing HFO-1123, HFO-1132(E), and HFC-32 as a raw material by a process consisting of a distillation step, an extractive distillation step, an extraction solvent recovery step, and a rectification step. Table 2 below shows the material balance in Example 2.

Distillation Step

A composition containing HFO-1123, HFO-1132(E), and HFC-32 was prepared as a distillation composition. The composition was supplied at a flow rate of 2030 mol/hr to a distillation column having the number of theoretical plates of 40 from the 20th stage from the top of the distillation column. The internal pressure of the distillation column is 0.5 MPaG, the column top is provided with a condenser, and the column bottom is provided with a reboiler.

The reboiler load and condenser load were adjusted so that HFC-32 with a purity of 50.0 mol % was distilled at 59.6 mol/hr from the top of the distillation column, and separation by distillation was performed. At this time, the condenser calorie was calculated to be 40616 kcal/hr, and the reboiler calorie was calculated to be 40617 kcal/hr.

As shown in Table 2, HFC-32 in the composition containing HFO-1123, HFO-1132(E), and HFC-32 was significantly reduced.

Extractive Distillation Step

The distillate (extractive distillation composition) extracted from the top of the distillation column was supplied at a flow rate of 59.6 mol/hr to an extractive distillation column having the number of theoretical plates of 40 from the 20th stage from the top of the extractive distillation column. Further, acetonitrile as an extraction solvent was supplied at a flow rate of 600.0 mol/hr (about 10 equivalents of the flow rate of the extractive distillation composition supplied to the extractive distillation column) to the extractive distillation column from the 5th stage from the top of the extractive distillation column. The internal pressure of the extractive distillation column is 0.5 MPaG, the top of the extractive distillation column is provided with a condenser, and the column bottom is provided with a reboiler.

The reboiler load and condenser load were adjusted so that a composition containing HFO-1123 with a purity of 33.5 mol % and HFO-1132(E) with a purity of 66.0 mol % was distilled at 29.9 mol/hr from the top of the extractive distillation column, and separation by distillation was performed. At this time, the condenser calorie was calculated to be 804 kcal/hr, and the reboiler calorie was calculated to be 2592 kcal/hr.

Figure 5:
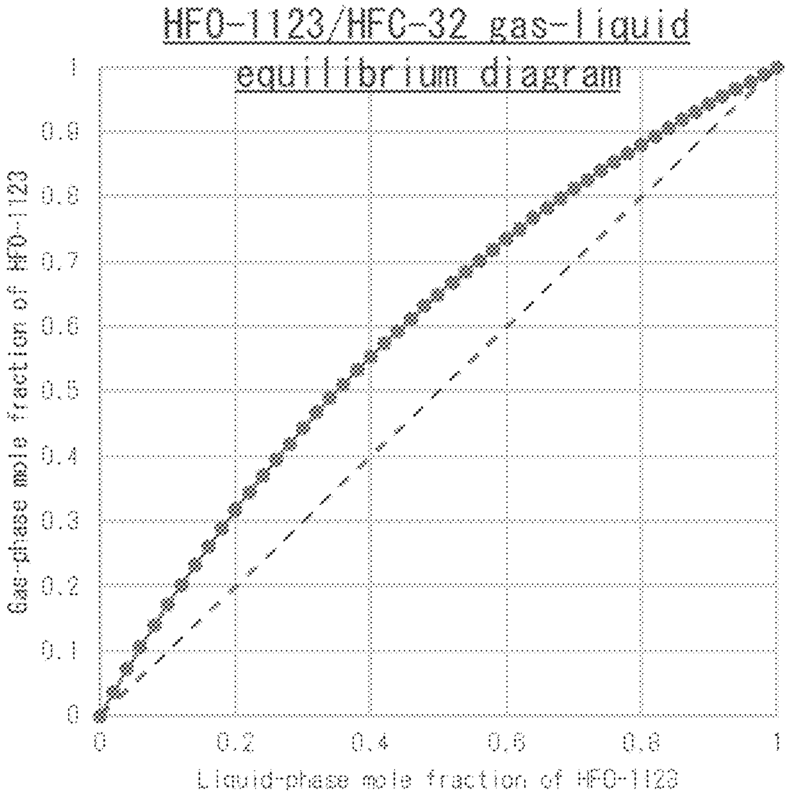
FIG. 5 is an HFO-1123/HFC-32 gas-liquid equilibrium diagram when using acetonitrile as an extraction solvent in the extractive distillation step of Example 2. The horizontal axis indicates the liquid-phase mole fraction of HFO-1123, and the vertical axis indicates the gas-phase mole fraction of HFO-1123.

FIG. 5 is an HFO-1123/HFC-32 gas-liquid equilibrium diagram when using about 10 equivalents of acetonitrile as an extraction solvent per equivalent of the extractive distillation composition. As shown in FIG. 5, it was confirmed that HFO-1123 and HFC-32 could be separated by performing a distillation operation at a pressure of 0.5 MPaG using acetonitrile as an extraction solvent.

Figure 6:
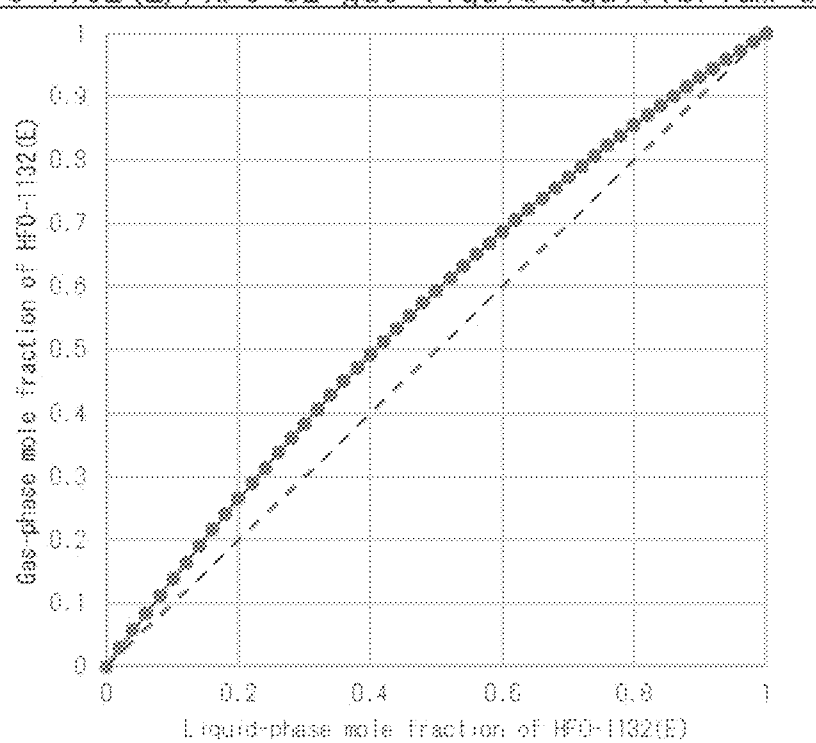
FIG. 6 is an HFO-1132(E)/HFC-32 gas-liquid equilibrium diagram when using acetonitrile as an extraction solvent in the extractive distillation step of Example 2. The horizontal axis indicates the liquid-phase mole fraction of HFO-1132 (E), and the vertical axis indicates the gas-phase mole fraction of HFO-1132(E).

FIG. 6 is an HFO-1132(E)/HFC-32 gas-liquid equilibrium diagram when using about 10 equivalents of acetonitrile as an extraction solvent per equivalent of the extractive distillation composition. As shown in FIG. 6, it was confirmed that HFO-1132(E) and HFC-32 could be separated by performing a distillation operation at a pressure of 0.5 MPaG using acetonitrile as an extraction solvent.

Extraction Solvent Recovery Step

The bottom product extracted from the column bottom in the extractive distillation step was supplied at a flow rate of 629.8 mol/hr (flow rate of HFO-1132(E): 0.1 mol/hr, flow rate of HFC-32: 29.7 mol/hr, and flow rate of acetonitrile: 600.0 mol/hr) to an extraction solvent recovery column having the number of theoretical plates of 10 (hereinafter simply referred to as "the recovery column") from the 5th stage from the top of the recovery column. The internal pressure of the recovery column is 0.5 MPaG, the column top is provided with a condenser, and the column bottom is provided with a reboiler.

The reboiler load and condenser load were adjusted so that HFC-32 with a purity of 96.8 mol % was distilled at 30.6 mol/hr from the top of the recovery column, and separation by distillation was performed. At this time, the condenser calorie was calculated to be 686 kcal/hr, and the reboiler calorie was calculated to be 1188 kcal/hr.

The bottom product containing acetonitrile extracted from the bottom of the recovery column (flow rate of acetonitrile: 600.0 mol/hr) was recirculated to the extractive distillation step for use.

Rectification Step

The distillate extracted from the column top in the extractive distillation step was supplied at a flow rate of 29.9 mol/hr to a rectification column having the number of theoretical plates of 40 from the 20th stage from the top of the rectification column. The internal pressure of the rectification column is 0.5 MPaG, the column top is provided with a condenser, and the column bottom is provided with a reboiler.

The reboiler load and condenser load were adjusted so that HFO-1123 with a purity of 89.7 mol % was distilled at 11.0 mol/hr from the top of the rectification column, and rectification was performed. At this time, the condenser calorie was calculated to be 925 kcal/hr, and the reboiler calorie was calculated to be 933 kcal/hr.

The results of the composition analysis of the obtained bottom product by gas chromatography revealed that HFO-1132(E) with a purity of 99.5 mol % was contained.

TABLE 2

| | ① | ② | ④ | ⑥ | ⑧ | ⑨ |
|---|---|---|---|---|---|---|
| Flow rate (mol/hr) | 2030 | 59.6 | 29.9 | 30.6 | 11.0 | 18.9 |
| Purity of HFO-1123 (mol %) | 0.5 | 16.8 | 33.5 | 0.0 | 89.7 | 0.5 |
| Purity of HFO-1132 (E) (mol %) | 1.0 | 33.2 | 66.0 | 0.2 | 8.9 | 99.5 |
| Purity of HFC-32 (mol %) | 98.5 | 50.0 | 0.5 | 96.8 | 1.3 | 0.0 |

Example 3

Figure 7:
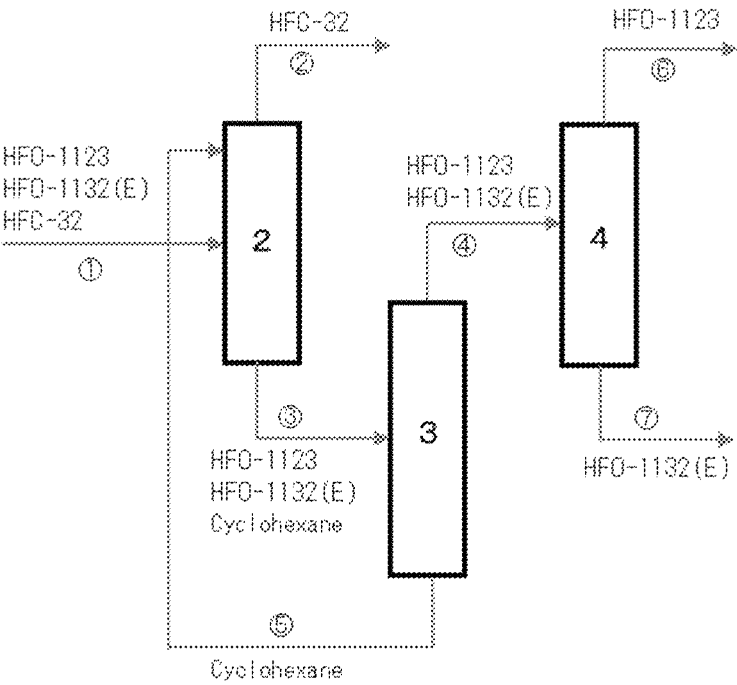
FIG. 7 is the outline of the process in Example 3.
Figure 8:
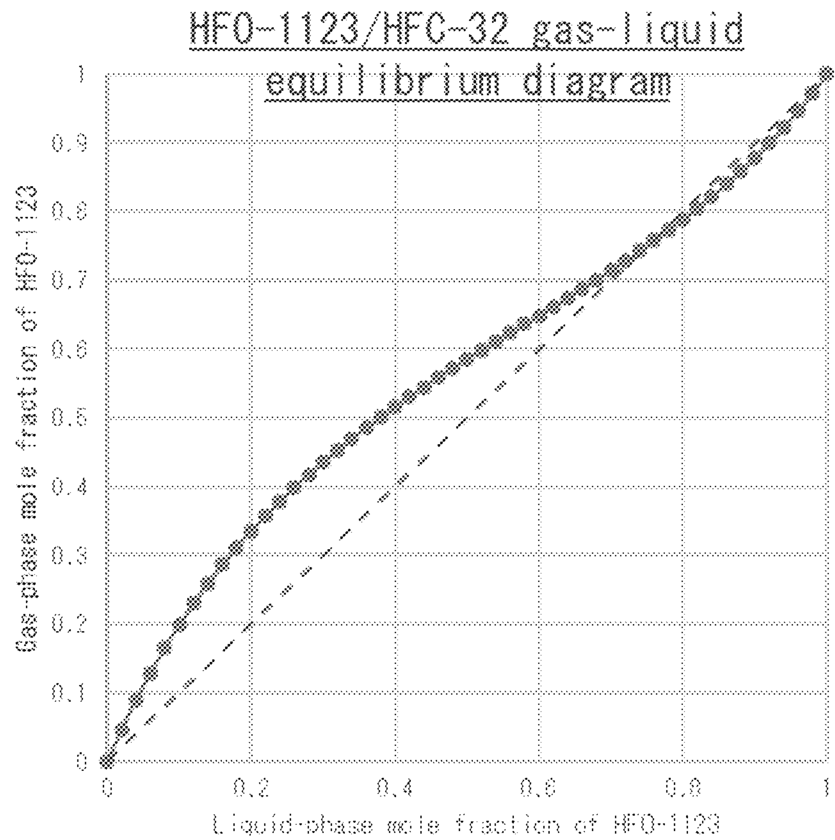
FIG. 8 is an HFO-1123/HFC-32 gas-liquid equilibrium diagram when using no extraction solvent. The horizontal axis indicates the liquid-phase mole fraction of HFO-1123, and the vertical axis indicates the gas-phase mole fraction of HFO-1123.
Figure 9:
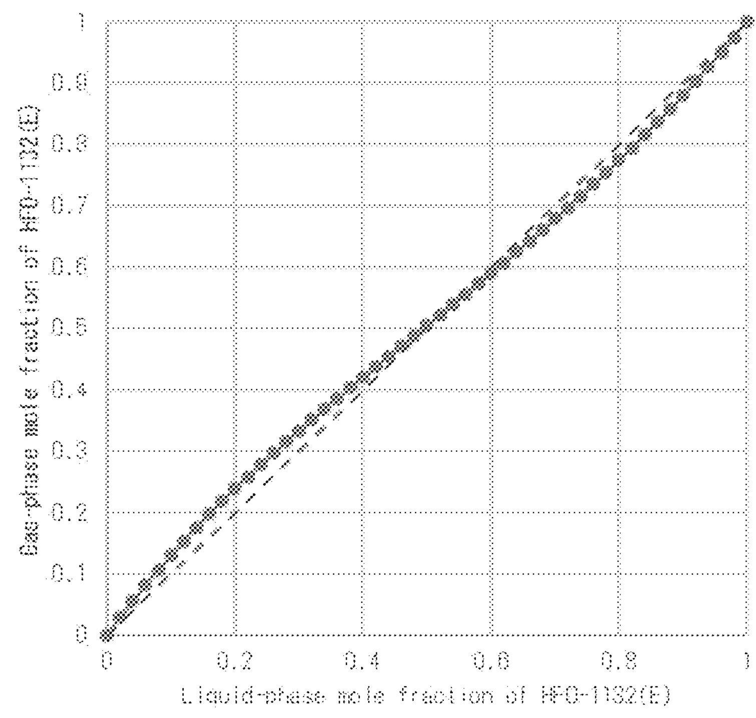
FIG. 9 is an HFO-1132(E)/HFC-32 gas-liquid equilibrium diagram when using no extraction solvent. The horizontal axis indicates the liquid-phase mole fraction of HFO-1132 (E), and the vertical axis indicates the gas-phase mole fraction of HFO-1132(E).

According to the flow diagram shown in FIG. 7, purified HFO-1132(E) and HFO-1123 were produced using a composition containing HFO-1123, HFO-1132(E), and HFC-32 as a raw material by a process consisting of an extractive distillation step, an extraction solvent recovery step, and a rectification step. Table 3 below shows the material balance in Example 3.

Extractive Distillation Step

A composition containing HFC-32, HFO-1132(E), and HFO-1123 was prepared as an extractive distillation composition. The composition was supplied at a flow rate of 2030 mol/hr to an extractive distillation column having the number of theoretical plates of 40 from the 20th stage from the top of the extractive distillation column. Further, cyclohexane as an extraction solvent was supplied at a flow rate of 20299.9 mol/hr (about 10 equivalents of the flow rate of the extractive distillation composition supplied to the extractive distillation column) to the extractive distillation column from the 5th stage from the top of the extractive distillation column. The internal pressure of the distillation column is 0.5 MPaG, the column top is provided with a condenser, and the column bottom is provided with a reboiler.

The reboiler load and condenser load were adjusted so that HFC-32 with a purity of 99.9 mol % was distilled at 2030 mol/hr from the top of the extractive distillation column, and separation by distillation was performed. At this time, the condenser calorie was calculated to be 51161 kcal/hr, and the reboiler calorie was calculated to be 176527 kcal/hr.

Extraction Solvent Recovery Step

The bottom product extracted from the column bottom in the extractive distillation step was supplied at a flow rate of 20328.2 mol/hr to an extraction solvent recovery column having the number of theoretical plates of 10 (hereinafter simply referred to as "the recovery column") from the 5th stage from the top of the extraction solvent recovery column. The internal pressure of the recovery column is 0.5 MPaG, the column top is provided with a condenser, and the column bottom is provided with a reboiler.

The reboiler load and condenser load were adjusted so that a composition containing HFO-1123 with a purity of 29.8 mol % and HFO-1132(E) with a purity of 70.1 mol % was distilled at 28.2 mol/hr from the top of the extraction solvent recovery column. At this time, the condenser calorie was calculated to be 24136 kcal/hr, and the reboiler calorie was calculated to be 25943 kcal/hr.

The bottom product containing cyclohexane extracted from the column bottom was recirculated to the extractive distillation step for use.

Rectification Step

The distillate extracted from the column top in the extraction solvent recovery step was supplied at a flow rate of 28.2 mol/hr to a rectification column having the number of theoretical plates of 40 from the 20th stage from the top of the rectification column. The internal pressure of the rectification column is 0.5 MPaG, the column top is provided with a condenser, and the column bottom is provided with a reboiler.

The reboiler load and condenser load were adjusted so that HFO-1123 with a purity of 89.1 mol % was distilled at 9.3 mol/hr from the top of the rectification column, and rectification was performed. At this time, the condenser calorie was calculated to be 667 kcal/hr, and the reboiler calorie was calculated to be 674 kcal/hr.

The results of the composition analysis of the obtained bottom product by gas chromatography revealed that HFO-1132(E) with a purity of 99.5 mol % was contained.

TABLE 3

| | ① | ② | ④ | ⑥ | ⑦ |
|---|---|---|---|---|---|
| Flow rate (mol/hr) | 2030 | 2001.7 | 28.2 | 9.3 | 18.9 |
| Purity of HFO-1123 (mol %) | 0.5 | 0.1 | 29.8 | 89.1 | 0.5 |
| Purity of HFO-1132(E) (mol %) | 1.0 | 0 | 70.1 | 10.6 | 99.5 |
| Purity of HFC-32 (mol %) | 98.5 | 99.9 | 0.1 | 0.3 | 0.0 |

Table 4 below shows the total calorie (kcal/hr) generated in the steps described in Examples 1, 2, and 3.

TABLE 4

| | Total calorie [kcal/hr] |
|---|---|
| Example 1 | 88926 |
| Example 2 | 88361 |
| Example 3 | 279108 |

As is clear from the results of Table 4, Examples 1 and 2 reduce the energy costs more than Example 3 and purify HFO-1132(E) and HFO-1123 to a high purity.

The present disclosure provides the invention according to the following embodiments.

Item 1. A method for producing purified trans-1,2-difluoroethylene (HFO-1132(E)) and/or 1,1,2-trifluoroethylene (HFO-1123), comprising:

a distillation step of distilling composition 1 comprising difluoromethane (HFC-32) and HFO-1132(E) and/or HFO-1123 to obtain composition 2 in which HFC-32 is reduced from composition 1; and an extractive distillation step of bringing composition 2 into contact with an extraction solvent to obtain a composition comprising HFO-1132(E) and/or HFO-1123, in which HFC-32 is reduced from composition 2, composition 2 being an azeotropic composition or azeotrope-like composition comprising HFC-32 and HFO-1132(E) and/or HFO-1123.

Item 2. The production method according to Item 1, wherein the distillation step is performed at a pressure of 0.05 to 5 MPaG (gauge pressure).

Item 3. A method for producing purified trans-1,2-difluoroethylene (HFO-1132(E)) and/or 1,1,2-trifluoroethylene (HFO-1123), comprising an extractive distillation step of bringing an azeotropic composition or azeotrope-like composition comprising difluoromethane (HFC-32) and HFO-1132(E) and/or HFO-1123 into contact with an extraction solvent to obtain a composition in which HFC-32 is reduced from the azeotropic composition or the azeotrope-like composition.

Item 4. The production method according to any one of Items 1 to 3, comprising a rectification step of rectifying the composition obtained in the extractive distillation step to separate it into a composition comprising HFO-1132(E) as a main component, and a composition comprising HFO-1123 as a main component.

Item 5. The production method according to any one of Items 1 to 4, comprising an extraction solvent recovery step of recovering the extraction solvent used in the extractive distillation step, and recirculating the recovered extraction solvent to the extractive distillation step.

Item 6. The production method according to any one of Items 1 to 5, wherein the extractive distillation step is performed at a pressure of 0.05 to 5 MPaG (gauge pressure).

Item 7. The production method according to any one of Items 1 to 6, wherein the extraction solvent is at least one compound selected from the group consisting of saturated hydrocarbon compounds, halogenated hydrocarbon compounds, nitrile compounds, ether compounds, ketone compounds, alcohol compounds, and ester compounds.

Item 8. The production method according to any one of Items 1 to 7, wherein the extraction solvent has a standard boiling point of 30 to 135° C.

Item 9. The production method according to any one of Items 1 to 8, wherein the extraction solvent is at least one compound selected from the group consisting of cyclohexane, carbon tetrachloride, acetonitrile, di-n-propyl ether, acetone, methanol, and ethyl acetate.

Item 10. An azeotropic or azeotrope-like composition comprising a refrigerant, the refrigerant comprising trans-1,2-difluoroethylene (HFO-1132(E)), 1,1,2-trifluoroethylene (HFO-1123), and difluoromethane (HFC-32), wherein the total concentration of the three components is 99.5 mass % or more based on the entire refrigerant, and the mass ratio of the three components in a ternary composition diagram having the three components as vertices falls within a region surrounded by a figure passing through the following 4 points:

point A (HFO-1132(E)/HFO-1123/HFC-32=39.6 mass %/1.5 mass %/58.9 mass %), point B (HFO-1132(E)/HFO-1123/HFC-32=64.5 mass %/1.4 mass %/34.1 mass %), point C (HFO-1132(E)/HFO-1123/HFC-32=0.9 mass %/70.2 mass %/28.9 mass %), and point D (HFO-1132(E)/HFO-1123/HFC-32=0.9 mass %/80.1 mass %/19.0 mass %).

REFERENCE SIGNS LIST

1: Distillation column

2: Extractive distillation column

3: Extraction solvent recovery column

4: Rectification column

The invention claimed is:

1. A method for producing purified trans-1,2-difluoroethylene (HFO-1132 (E)) and 1,1,2-trifluoroethylene (HFO-1123), comprising:

a distillation step of distilling a composition 1 comprising difluoromethane (HFC-32) and HFO-1132 (E) and HFO-1123 to obtain a composition 2 in which HFC-32 is reduced from composition 1; and an extractive distillation step of bringing composition 2 into contact with an extraction solvent to obtain a composition comprising HFO-1132 (E) and HFO-1123, in which HFC-32 is reduced from composition 2, wherein composition 2 is composition 2 being an azeotropic composition or azeotrope-like composition comprising HFC-32 and HFO-1132 (E) and HFO-1123, and wherein the extraction solvent is at least one compound selected from the group consisting of n-pentane, n-hexane, n-heptane, n-octane, cyclopentane, cyclohexane, cycloheptane, benzene, toluene, dichloromethane, trichloromethane, tetrachloromethane (carbon tetrachloride), 1,1-dichloroethane, 1,2-dichloroethane, 1,1,1-trichloroethane, 1,1,2-trichloroethane, acetonitrile, propanenitrile, isobutyronitrile, di-n-propyl ether, diisopropyl ether, 2-methoxy-2-methylpropane, 2-ethoxy-2-methylpropane, acetone, diethyl ketone, methyl ethyl ketone, methyl isobutyl ketone, cyclopentanone, methanol, ethanol, 1-propanol, 2-propanol, 1-butanol (n-butyl alcohol), 2-methyl-1-propanol (i-butyl alcohol), 2-butanol (sec-butyl alcohol), 2-methyl-2-propanol (t-butyl alcohol), methyl acetate, ethyl acetate, propyl acetate, isopropyl acetate, and butyl acetate.

2. The method according to claim 1, wherein the distillation step is performed at a pressure of 0.05 to 5 MPaG (gauge pressure).

3. The method according to claim 1, further comprising a rectification step of rectifying the composition obtained in the extractive distillation step to separate it into a composition comprising HFO-1132 (E) as a main component, and a composition comprising HFO-1123 as a main component.

4. The method according to claim 1, further comprising an extraction solvent recovery step of recovering the extraction solvent used in the extractive distillation step, and recirculating the recovered extraction solvent to the extractive distillation step.

5. The method according to claim 1, wherein the extractive distillation step is performed at a pressure of 0.05 to 5 MPaG (gauge pressure).

6. The method according to claim 1, wherein the extraction solvent is at least one compound selected from the group consisting of cyclohexane, carbon tetrachloride, acetonitrile, di-n-propyl ether, acetone, methanol, and ethyl acetate.

7. The method according to claim 2, wherein the extraction solvent is at least one compound selected from the group consisting of cyclohexane, carbon tetrachloride, acetonitrile, di-n-propyl ether, acetone, methanol, and ethyl acetate.

8. The method according to claim 1, wherein the extraction solvent is n-pentane, n-hexane, n-heptane, n-octane, cyclopentane, cyclohexane, cycloheptane, benzene, toluene, dichloromethane, trichloromethane, tetrachloromethane (carbon tetrachloride), 1,1-dichloroethane, 1,2-dichloroethane, 1,1,1-trichloroethane, 1,1,2-trichloroethane, acetonitrile, propanenitrile, isobutyronitrile, di-n-propyl ether, diisopropyl ether, 2-methoxy-2-methylpropane, 2-ethoxy-2-methylpropane, acetone, diethyl ketone, methyl ethyl ketone, methyl isobutyl ketone, cyclopentanone, methanol, ethanol, 1-propanol, 2-propanol, 1-butanol (n-butyl alcohol), 2-methyl-1-propanol (i-butyl alcohol), 2-butanol (sec-butyl alcohol), 2-methyl-2-propanol (t-butyl alcohol), methyl acetate, ethyl acetate, propyl acetate, isopropyl acetate, or butyl acetate.

9. A method for producing purified trans-1,2-difluoroethylene (HFO-1132 (E)) and 1,1,2-trifluoroethylene (HFO-1123), comprising an extractive distillation step of bringing an azeotropic composition or azeotrope-like composition comprising difluoromethane (HFC-32) and HFO-1132 (E) and HFO-1123 into contact with an extraction solvent to obtain a composition in which HFC-32 is reduced from the azeotropic composition or the azeotrope-like composition, wherein the extraction solvent is at least one compound selected from the group consisting of cyclohexane, carbon tetrachloride, acetonitrile, di-n-propyl ether and ethyl acetate.

10. The method according to claim 9, further comprising a rectification step of rectifying the composition obtained in the extractive distillation step to separate it into a composition comprising HFO-1132 (E) as a main component, and a composition comprising HFO-1123 as a main component.

11. The method according to claim 9, further comprising an extraction solvent recovery step of recovering the extraction solvent used in the extractive distillation step, and recirculating the recovered extraction solvent to the extractive distillation step.

12. The method according to claim 9, wherein the extractive distillation step is performed at a pressure of 0.05 to 5 MPaG (gauge pressure).

* * * * *